United States Patent [19]

Alchas

[11] Patent Number: 4,537,593
[45] Date of Patent: Aug. 27, 1985

[54] SELF-VENTING, NON-CORING NEEDLE ASSEMBLY

[75] Inventor: Paul G. Alchas, Montclair, N.J.

[73] Assignee: Becton, Dickinson and Co., Paramus, N.J.

[21] Appl. No.: 501,303

[22] Filed: Jun. 6, 1983

[51] Int. Cl.³ .............................................. A61M 5/00
[52] U.S. Cl. .................................. 604/411; 604/274; 604/414
[58] Field of Search .................. 604/411, 274, 86, 88, 604/184, 244, 412, 414, 415; 222/81

[56] References Cited

U.S. PATENT DOCUMENTS

| | | | |
|---|---|---|---|
| 2,904,405 | 9/1959 | Owings | 604/274 |
| 2,973,758 | 3/1961 | Murrish . | |
| 3,063,451 | 11/1962 | Kowalk | 604/411 |
| 3,469,572 | 9/1969 | Nehring . | |
| 3,602,272 | 8/1971 | Stawski . | |
| 3,608,550 | 9/1971 | Stawski . | |
| 3,941,171 | 3/1976 | Ogle . | |
| 4,058,121 | 11/1977 | Choski . | |
| 4,296,786 | 10/1981 | Brignola . | |

Primary Examiner—Stephen C. Pellegrino
Attorney, Agent, or Firm—John L. Voellmicke

[57] ABSTRACT

A self-venting, non-coring needle assembly for the transfer of liquid to or from a container includes a hub having a forward end, a rearward end for engaging fluid transfer apparatus and a passageway therethrough. A hollow shaft extends outwardly from the forward end of the hub and has a lumen in fluid communication with the passageway. The shaft includes a closed distal end and an aperture in the side thereof near the distal end and in fluid communication with the lumen. A sleeve is slidably maintained on the shaft. During use, gases are vented by passing freely between the outside of the shaft and the inside dimension of the sleeve.

20 Claims, 19 Drawing Figures

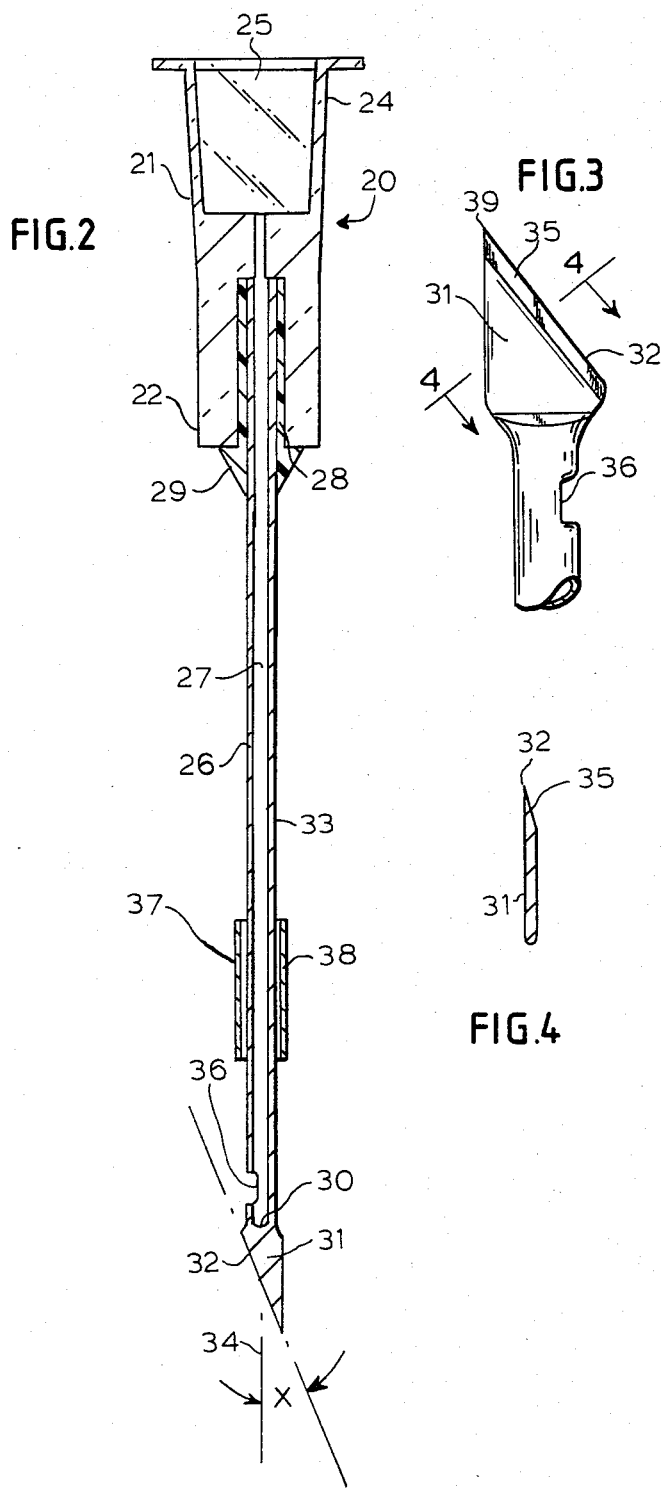

SELF-VENTING, NON-CORING NEEDLE ASSEMBLY

BACKGROUND OF THE INVENTION

1. Field of the Invention

The present invention relates to a needle assembly and more particularly concerns a self-venting, non-coring needle assembly for the transfer of liquid to or from a container having a needle penetrable stopper thereon.

2. Description of the Prior Art

Liquid medication, for injection and intravenous applications, is commonly available in rigid containers having a closure with an elastomeric needle penetrable stopper. Frequently the amount of liquid medication in these containers is in excess of the amount required for each individual dose. Accordingly, it is the task of a hospital pharmacy, for example, to transfer the liquid medication from the larger container to smaller containers, also with needle penetrable stoppers, such as I.V. bottles or to other storage or delivery devices such as syringes. This type of transfer is also required where the medication has a short shelf life and must be mixed just prior to use, for example using a syringe for adding sterile water to a vial containing lyophilized medication. Since sterility of the medication is desired, the vial to vial, syringe to vial, or vial to syringe transfer is usually performed in a laminar flow hood. Transfer of liquid medication to and from these vials requires not only piercing the stopper to provide a path for the medication but also piercing the stopper to provide a path for air to escape or enter the vial so that the medication will flow freely.

Prior art devices for the aforementioned transfer of liquids are fraught with problems. For example, a hollow pointed shaft or needle for piercing a vial stopper, as will be explained in greater detail hereinafter, may cause coring. Coring results from the needle not only piercing the stopper but also cutting a core of stopper material with the relatively sharp edges found at the intersection of the inside diameter of the needle and the surface at the end of the needle. These cores represent a potential health hazard if they pass along with the liquid medication into the patient's body. Also, if the cores are large enough or if there are many of them, the stopper may not retain enough material to effectively seal the vial in order to prevent leakage or to protect sterility. In addition, if the device used to puncture the stopper is too large, it may damage the stopper, even in the absence of any coring, by ripping or tearing the stopper so that it no longer effectively seals the vial. Non-coring puncture devices without venting capability are also available, but are of limited use in transferring liquid to or from a vial with a pierceable stopper unless two or more of these devices are used.

Both Ogle (U.S. Pat. No. 3,941,171) and Brignola (U.S. Pat. No. 4,296,786) teach fluid transfer devices wherein most embodiments include a central body portion with large spike like projections extending outwardly from each side of the central portion. The spikes contain a pair of common longitudinally staggered parallel passages extending from the tip of one spike to the tip of the other. Since the passageways terminate at the end surface of the spikes, these devices have the potential of producing up to four cores with each vial to vial transfer. Also, the large spike size required by parallel passageways increases the potential for stopper damage and requires higher forces for penetration into the stopper. This type of device is only suitable for vial to vial transfer.

Similar to the above described inventions, Murrish (U.S. Pat. No. 2,973,758) teaches a device with a central member with two spaced needles projecting from one side thereof. One of these needles passes through the member and projects from the other side. The other needle vents to the other side of the member but does not project outwardly therefrom. Here again, for piercing and venting, two separate punctures are required, with two chances for producing cores. Also, none of the above-mentioned patents teaches a device which can be used in conjunction with a syringe or tubing with luer fittings.

Stawski (U.S. Pat. No. 3,608,550) teaches a transfer needle assembly for use in transferring liquid medication from a vial with a pierceable stopper to a plurality of syringes. Stawski shows a device with two cannulae, each having its own hub. The larger diameter cannula is used to pierce the rubber stopper and then the smaller diameter cannula slides through the larger cannula to contact the liquid in the vial. Venting takes place between the outside diameter of the smaller cannula and the inside diameter of the larger cannula. The Stawski transfer needle offers an improvement over the above-mentioned devices in that there is only one puncture which can potentially produce a core from the stopper. However, the Stawski device is primarily intended for the limited use of filling syringes and is more time-wise efficient when used with external apparatus which positions the transfer needle, but is not part of the fluid path. This external apparatus is taught by Stawski in U.S. Pat. No. 3,602,272.

Murphy (U.S. Pat. No. 2,541,272) teaches a needle for filling and exhausting ampules and, like Stawski, the Murphy needle has two hubs and one point for potential generation of cores. Murphy shows an outer sleeve which is tapered toward and anchored to the inner needle at the end of sleeve furthest from the hubs. The sleeve contains venting ports in its side and in its hub.

Choksi et al. (U.S. Pat. No. 4,058,121) teach a thermoplastic needle for injecting sterile liquid into a vial. This needle is in the shape of a plastic spike with an external vent groove running along the length of the spike. Liquid leaves the spike through two side ports therein. Choksi et al. eliminates coring by providing a pointed tip, however, the side ports, which are formed in the tapered portion of the tip, may contribute to tearing small pieces of the stopper loose as the spike moves through the stopper. Also, the apparently large cross-section can contribute to stopper damage. The external venting groove would appear to present a potential problem in that rotation of the spike along its longitudinal axis, while it is inserted in a flexible stopper, may cause parts of the stopper, along the puncture hole, to enter the groove and reduce or terminate venting capacity.

Also known is the VACUTAINER brand Multiple Sample Needle as shown in a products catalog of Becton, Dickinson and Company. This needle has two opposed cannula communicating with a central external screw thread hub. The hub is intended to be screwed into a cylindrical holder after which the first cannula, which projects outwardly from the hub, is inserted in a patient's vein. Then, an evacuated glass tube with a pierceable stopper is forceably slid into the cylindrical holder until the second cannula, which projects into the holder, pierces and passes through the evacuated tube stopper. At this point there is fluid communication between the patient's vein and the evacuated glass tube, and blood is drawn from the patient into the tube by the vacuum forces therein created. The second cannula is non-coring and has a compressed end which is cut off at an angle to the longitudinal axis of the cannula and an aperture in its side which communicates with the lumen therein. The second cannula does not have any venting structure and, because of its use, must not allow venting to the atmosphere which would reduce the vacuum forces needed to draw the blood from the patient.

The transfer of liquid to or from a container or vial with closure having an elastomeric needle penetrable stopper has been addressed by the prior art. However, there is still a need for a simple, straight-forward, reliable, easily fabricated self-venting, non-coring needle assembly which allows transfer of liquid to and from a vial with a pierceable stopper while incurring minimal stopper damage and requiring minimal penetration forces. It is also desirable that the needle assembly be operable without the use of an external apparatus which is not part of the fluid path.

SUMMARY OF THE INVENTION

The self-venting, non-coring needle assembly of the present invention comprises a hub having a forward end, a rearward end adapted to engage external fluid transfer apparatus and a passageway therethrough. A hollow shaft extends outwardly from the forward end of the hub. This shaft has a lumen which is in fluid communication with the hub passageway and a closed distal end. An aperture in the side of the shaft adjacent to the distal end is in fluid communication with the lumen. A sleeve is slidably maintained on the shaft. Venting means is provided for allowing gas to pass between the outside of the shaft and the inside of the sleeve.

In accordance with another embodiment of the present invention, a self-venting, non-coring needle assembly for the transfer of liquid to or from a container having a needle penetrable stopper thereon includes a rigid hub having a forward end, a rearward end adapted to engage external fluid transfer apparatus and a passageway therethrough. A cannula extends outwardly from the forward end of the housing and terminates in a closed distal end. The cannula has a lumen which is in fluid communication with the passageway of the hub. This cannula also contains a flat portion at its distal end which is substantially parallel to the longitudinal axis of the cannula and is larger along its major dimension than the outside diameter of the cannula. Also, the flat portion terminates in a straight edge lying at an angle to the longitudinal axis of the cannula. An aperture, which is in fluid communication with the lumen, is positioned in the side wall of the cannula adjacent to the distal end. Also included is circularly shaped sleeve member surrounding the cannula and slidably engaged thereon. The sleeve member is shorter in length than the distance between the aperture and the forward end of the hub. The inside diameter of the sleeve is larger than the outside diameter of the cannula to allow gas to pass therebetween and smaller than the flat portion along its major axis so that the sleeve is prevented from sliding off the distal end of the cannula. Also, the inside diameter of the sleeve member is smaller than the hub so that the sleeve is prevented from sliding off the cannula at its proximal end.

In accordance with the principles of the present invention, a number of advantages and objectives are attained. Primarily, the present invention provides a simple straight forward self-venting, non-coring needle assembly which allows transfer of liquid to and from a vial with a pierceable stopper. The flat portion of the closed distal end of the cannula provides a non-coring stopper piercing point which also minimizes penetration forces and stopper damage during insertion of the cannula into the stopper. The sleeve member also contributes to the non-coring aspect of the present invention by entering the same hole in the stopper as made by the cannula. During use, gases are vented by passing between the outside of cannula and the inside dimension of the sleeve. The present invention is also operable without the use of external apparatus which is not part of the fluid path.

BRIEF DESCRIPTIONS OF THE DRAWINGS

FIG. 2 is a cross-sectional view of the self-venting, non-coring needle assembly of FIG. 1 taken along line 2—2;

FIG. 3 is a partial enlarged side elevation view of the distal end of the cannula of the preferred self-venting, non-coring needle assembly;

FIG. 4 is a cross-sectional view of the cannula of FIG. 3 taken along line 4—4;

DETAILED DESCRIPTION

Figure 1:
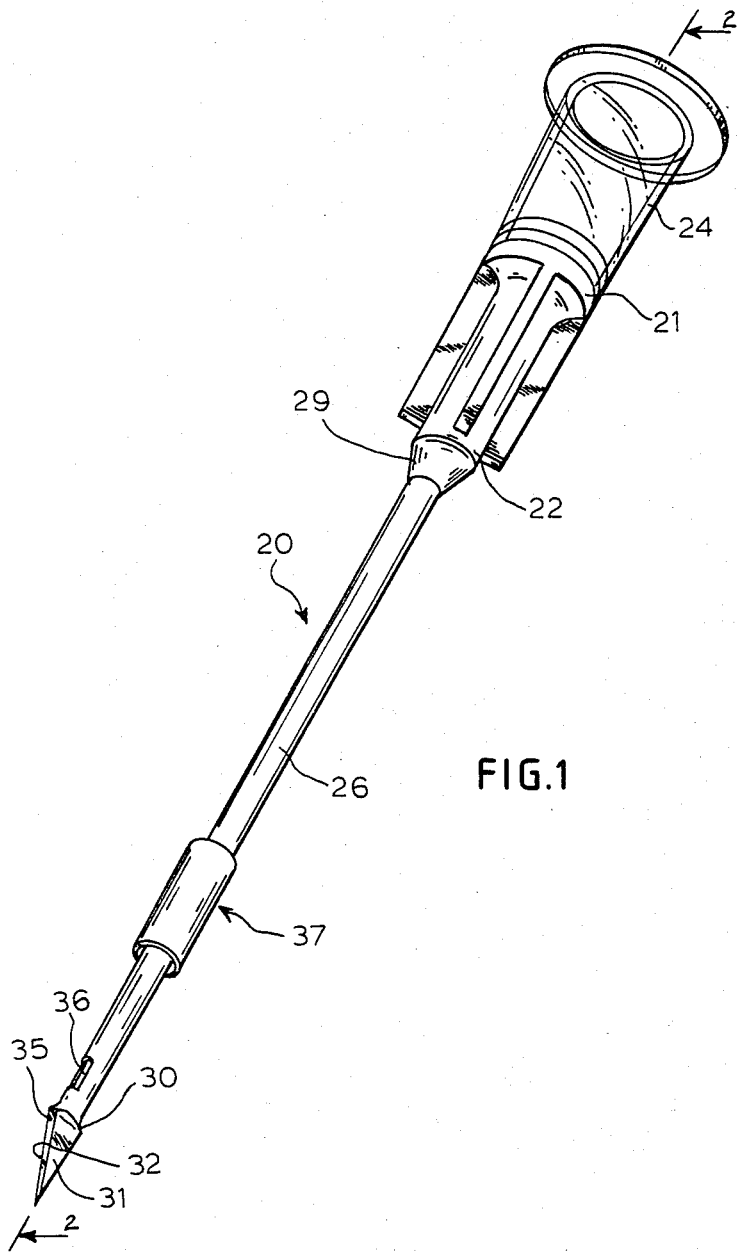
FIG. 1 is an enlarged perspective view of the preferred self-venting, non-coring needle assembly of the present invention.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 though 4, a self-venting, non-coring needle assembly 20 includes a rigid hub 21 having a forward end 22, a rearward end 24 and a passageway 25 therethrough. The rearward end is shaped to accept the standard luer tip of a syringe or other apparatus such as a tubing fitting with a tapered luer tip. A cannula 26 having a lumen 27 is connected to the hub so that the lumen is in fluid communication with the passageway. In the preferred embodiment, the forward end of the hub contains a recess 28, larger in diameter than the cannula, running along the longitudinal axis of the hub in fluid communication with the passageway. Space between the outside of the cannula and the inside of the recess is filled with epoxy 29 to fixedly contain the cannula within the hub. It will be apparent to one skilled in the art that numerous constructions can be used to join a cannula and a hub and that the arrangement described above is exemplary of these many possibilities. Also, it is within the purview of this invention to include a one-piece needle and hub assembly.

For descriptive purposes, locations indicated as "distal" are further from the user than locations on the same component indicated as "proximal." A closed distal end 30 of the cannula includes a compressed planar or flat portion 31 which is substantially parallel to a longitudinal axis 34 of the cannula and larger along its major dimension than outside diameter 33 of the cannula. Further, the planar portion terminates at a straight edge 32 lying at an angle to longitudinal axis 34. It is preferred that lesser included angle X between edge 32 and longitudinal axis 34 be between about twenty to sixty degrees with the preferred embodiment shown at thirty degrees. It is also preferred that flat portion 31 include a tapered portion 35 which is tapered toward straight edge 32 in a razor-like fashion.

Cannula 26 also includes an aperture 36 in the side wall thereof adjacent to closed distal end 30. This aperture is in fluid communication with lumen 27. In the preferred embodiment, aperture 36 is positioned below and substantially in alignment with edge 32, as seen in FIG. 3. Further included is a circularly shaped sleeve member 37 surrounding the cannula and slidably engaged thereon. The sleeve is preferably in the form of a cylinder with an inside diameter 38 larger than outside diameter 33 of cannula 26. Accordingly, the sleeve is freely slidable along the length of the cannula. However, the inside diameter of sleeve 37 is smaller than flat portion 31, when measured along the major axis of the flat portion, so that the sleeve is prevented from sliding off the closed distal end of the cannula. The inside diameter of the sleeve is also smaller than at least one portion of the hub, when measured in a direction transverse to the longitudinal axis of the cannula, so that the sleeve is prevented from sliding off the cannula at its proximal end. Sleeve member 37, as measured in a direction along the longitudinal axis thereof, should preferably be shorter than the distance between aperture 36 and hub 21 so that sleeve member 37 will not interfere with fluid flow through the aperture. Also, as will later become evident, it is preferred that sleeve member 37 be longer than the thickness of the stopper being pierced by the needle assembly.

Figure 6:
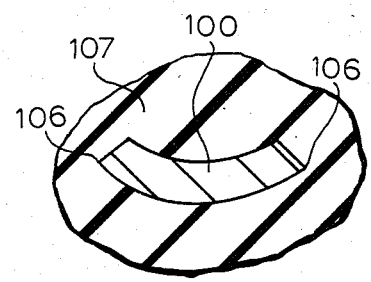
FIG. 6 is a cross-sectional view of the needle of FIG. 5 taken along line 6—6 as the needle initially penetrates a vial stopper.
Figure 5:
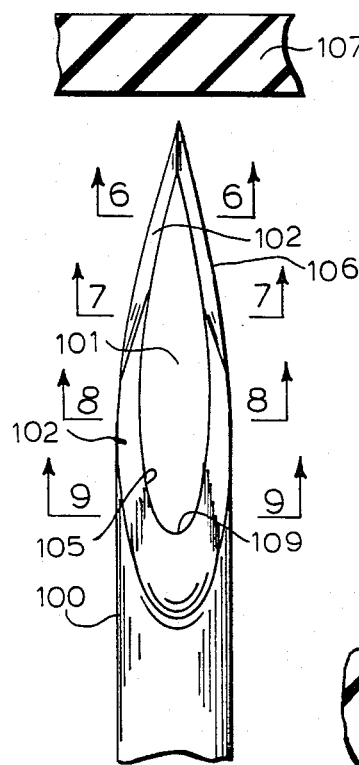
FIG. 5 is an enlarged partial side elevation view of a known and used needle shown in relative proximity to a partial enlarged cross-sectional side elevation view of a pierceable vial stopper.
Figure 7:
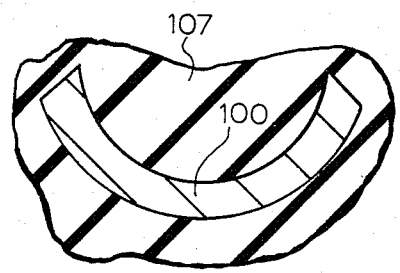
FIG. 7 is a cross-sectional view of the needle of FIG. 5 taken along line 7—7 as the needle further penetrates a vial stopper.
Figure 9:
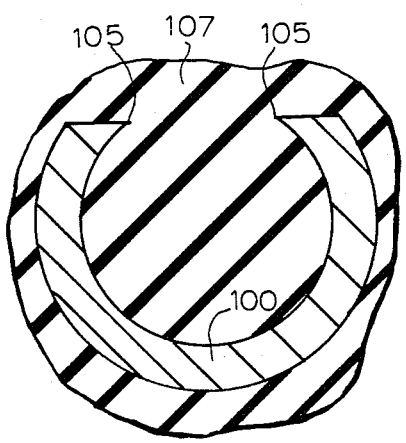
FIG. 9 is a cross-sectional view of the needle of FIG. 5 taken along line 9—9 as the needle still further penetrates a vial stopper.
Figure 8:
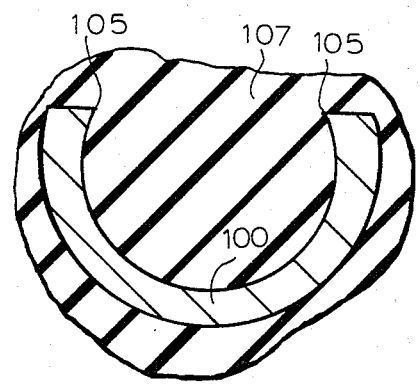
FIG. 8 is a cross-sectional view of the needle of FIG. 5 taken along line 8—8 as the needle still further penetrates a vial stopper.

As best shown in FIGS. 5 through 9, previously known and used needle 100 includes lumen 101 which acts as a fluid path, planar surface 102 which terminates in point 104, interior sharp edges 105, and exterior sharp edges 106. This type of needle, while commonly used for injecting medication into a human patient is also used to transfer medication to or from a vial. The sharp point and cutting edges easily penetrate human flesh. However, when needle 100 and similar needles are used to pierce stoppers on medication vials, they have a potential for cutting circular cores of stopper material out of the stopper with their interior edges 105. As best shown in FIG. 6, as needle 100 penetrates a stopper 107, it starts to cut an arcuate slit into the stopper. As the needle further penetrates the stopper, the cut becomes more and more circular as seen in FIGS. 7 through 9. It can be seen that interior edges 105, with respect to the stopper surface, come closer together as the depth of needle penetration increases, pinching and slicing the stopper material until the circle is complete at heel 109. At this point a separate piece of material, a core, can be cut out of the stopper. This core represents a potential health hazard if it finds its way into the patient. Also, the removal of the core material compromises the ability of the stopper to protect the sterility of the liquid in the vial and to prevent leaking. It should be pointed out, however, that not every penetration of a stopper by a needle like needle 100 produces a core. Also, edges may be dulled and lubricants added to reduce the tendency to core, but the potential exists.

Referring once again to FIGS. 3 and 4, it can be seen that the preferred embodiment of the instant invention includes a point 39 and slicing edge 32 to provide the ease of penetration of known needles but without the interior edges to potentially generate cores. Accordingly, the instant cannula is designed to puncture, slit and spread the stopper material and to allow it to return to its initial position after the cannula is removed. In order to reduce penetration forces and to minimize damage to the stopper, it is desirable to make the outside diameter of cannual 26 as small as possible. In the preferred embodiment, the cannula outside diameter is approximately 0.050 inch (1.27 mm).

Figure 10:
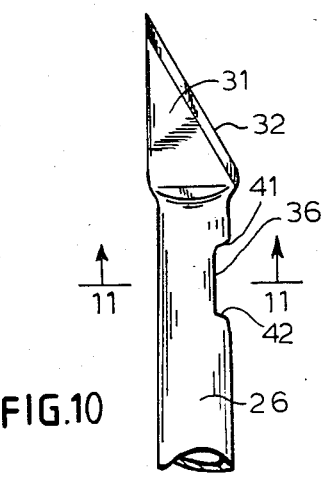
FIG. 10 is an enlarged partial side elevation view of the cannula of the preferred self-venting, non-coring needle assembly.
Figure 11:
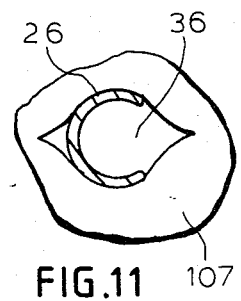
FIG. 11 is a cross-sectional view of the cannula of FIG. 10 taken along line 11—11 as the cannula penetrates a vial stopper.

Referring now to FIGS. 10 and 11, in order to further reduce the potential for removing portions of stopper 107, during penetration and removal of the cannula, it is preferred to orient aperture 36 so that it is below and substantially in alignment with edge 32 as seen in FIG. 10. With this orientation, aperture 36 is positioned to intersect the plane of the slit cut in the stopper by edge 32 of flat portion 31. Therefore, as cannula 26 penetrates or is removed from stopper 107, there will be less tendency for upper edge 41 and lower edge 42 of aperture 36 to scrape and remove stopper material from the inside of the slit in the stopper made by the preferred cannula.

Figure 12:
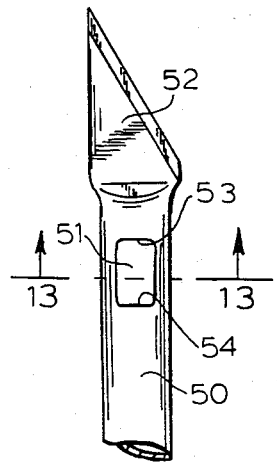
FIG. 12 is an enlarged partial side elevation view of the cannula of another embodiment of the self-venting, non-coring needle assembly.
Figure 13:
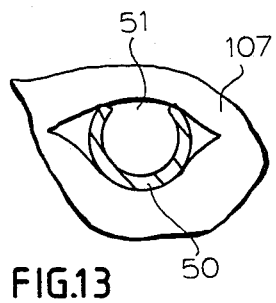
FIG. 13 is a cross-sectional view of the cannula of FIG. 12 taken along line 13—13 as the cannula penetrates a vial stopper.

Referring to FIGS. 12 and 13, alternative cannula 50 with aperture 51, below and substantially in alignment with flat portion 52, and with upper edge 53 and lower edge 54, may have a tendency to scrape and remove material from the inside of the slit in stopper 107 made by flat portion 52. Accordingly, this position for the aperture while acceptable, is not preferred.

Figure 14:
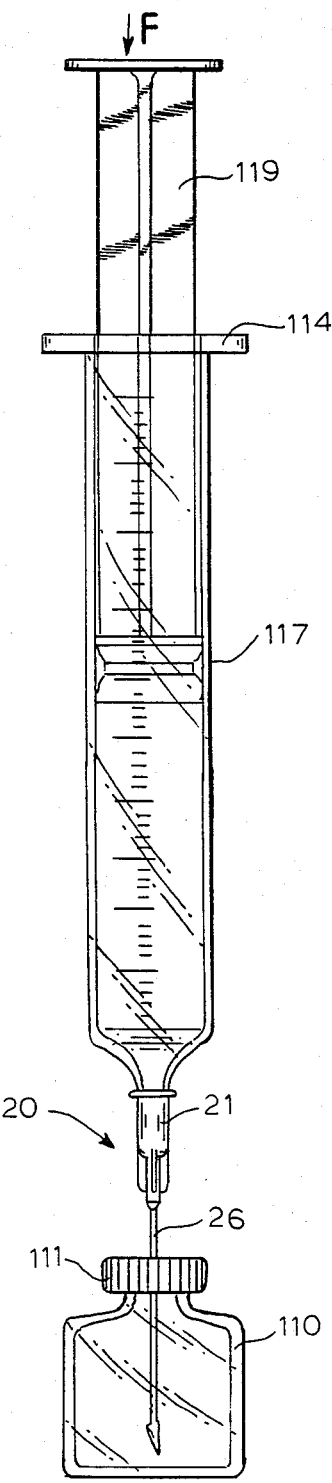
FIG. 14 is a side elevation view of the preferred self-venting, non-coring needle assembly being used with a hypodermic syringe to fill a liquid container having a needle penetrable stopper thereon.
Figure 15:
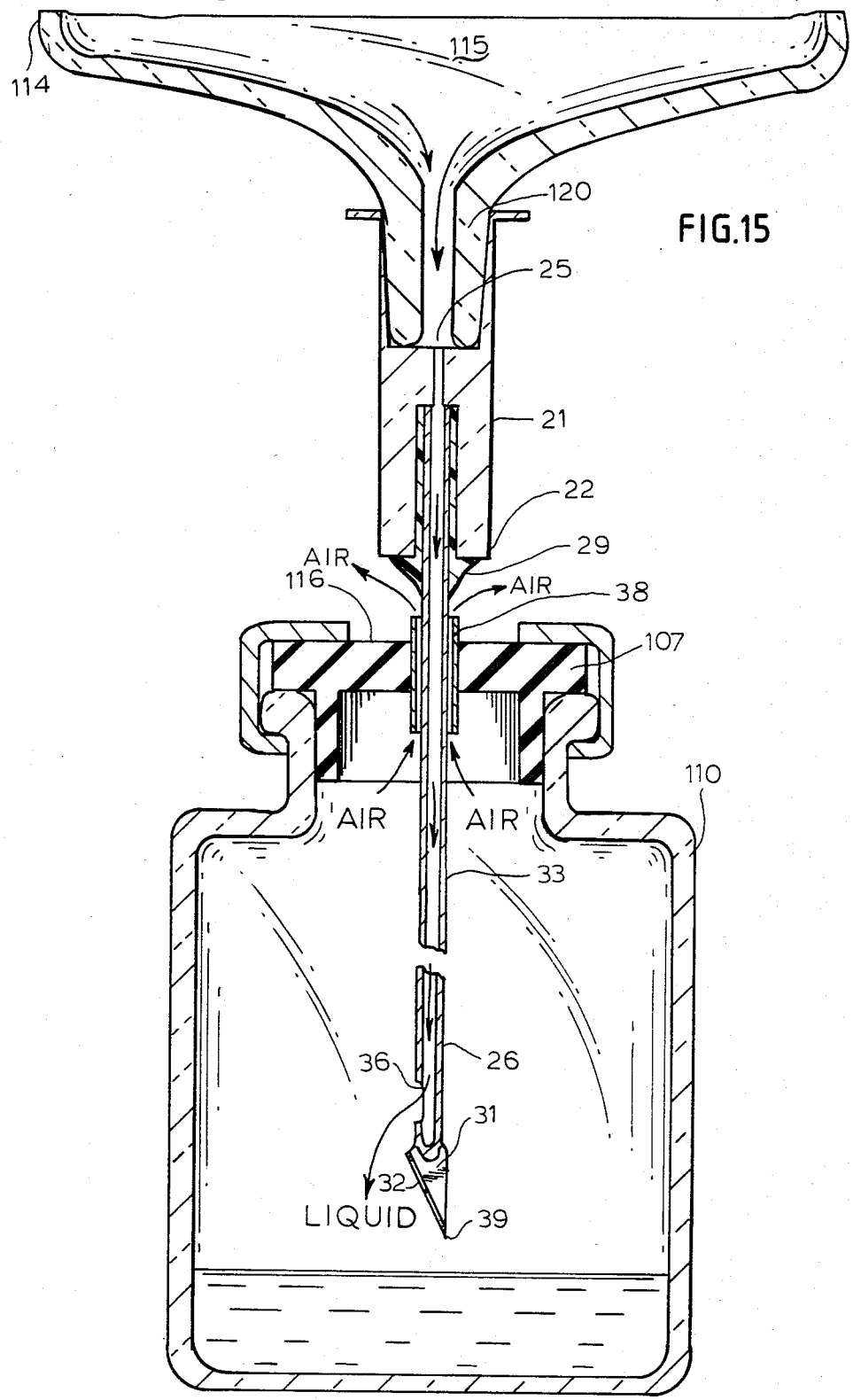
FIG. 15 is an enlarged cross-sectional view of the syringe, needle assembly and vial of FIG. 14.

FIGS. 14 and 15 depict the preferred self-venting, non-coring needle assembly of the present invention in use adding liquid, such as liquid medication or sterile water, to a vial 110 having a closure 111 with a needle penetrable stopper 107 thereon. Initially, self-venting, non-coring needle assembly 20 is attached to a syringe 114 containing liquid 115. The syringe, with needle assembly 20 attached, is positioned with the point of cannula 26 resting on top surface 116 of the stopper. Syringe barrel 117 is forced downwardly causing cannula 26 to pierce stopper 107. As the cannula passes through the stopper, sleeve 37 is forced along the cannula toward hub 21 until it contacts epoxy 29 or forward end 22 of the hub, depending on how large the diameter of the sleeve is and/or how much epoxy is used. At this point, the sleeve is forced through the hole in the stopper created by cannula 26 and the needle assembly is positioned as shown in FIGS. 14 and 15. To inject liquid into the vial, the user simultaneously holds syringe barrel 117 while applying force F to plunger rod 119. As the plunger rod moves toward needle assembly 20, liquid is forced out of syringe barrel tip 120, through passageway 25 in the hub, through cannula 26 and out of aperture 36 into the vial. Pressure inside the vial is increased as liquid is added. This increased pressure may eventually prevent introduction of further liquid into the vial, damage the stopper and/or force liquid out through existing slits in the stopper. However, the instant invention prevents pressure build-up by allowing pressurized air, contained within the vial, to exit through the space between outside diameter 33 of cannula 26 and inside diameter 38 of sleeve 37. It is desirable to make the diameters of the sleeve as small as possible in order to prevent possible coring by the sleeve as it passes through the hole in the stopper made by the cannula and also to prevent damage to the stopper. In the preferred embodiment, the inside diameter of sleeve 37 is approximately 0.058 inch (1.47 mm) which is 0.008 inch (0.2 mm) larger than the preferred outside diameter of cannula 26, and the outside diameter of the sleeve is approximately 0.070 inch (1.78 mm). In order to provide an unobstructed exit path for the air in the vial, it is preferred that sleeve 37 be longer than the thickness of the vial stopper at the point of cannula penetration. A sleeve length of approximately 0.25 inch (6.35 mm) is satisfactory for most applications.

The instant invention can also be used to remove liquid from a vial. However, when emptying a vial, aperture 36 should be kept below the liquid level in the vial. Since emptying reduces the pressure in the vial, outside air will now enter the vial through the space between inside diameter 38 of the sleeve member and outside diameter 33 of the cannula.

Another possible use of the instant invention is in withdrawing sterile water from a vial with a pierceable stopper into a syringe and then placing smaller quantities of water into each of many smaller vials containing lyophilized medication which requires water for activation. This entire operation can be accomplished with one needle assembly of the present invention rather than, for example, several needles, a valve and tubing.

Figure 16:
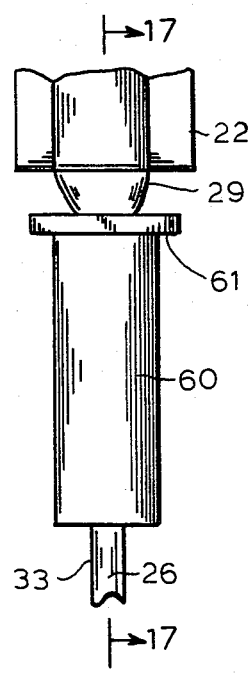
FIG. 16 is an enlarged partial side elevation view of an alternative embodiment of the present self-venting, non-coring needle assembly.
Figure 17:
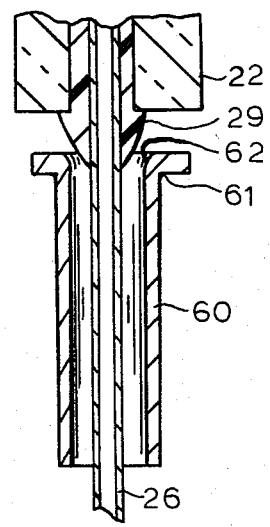
FIG. 17 is a cross-sectional view of the self-venting, non-coring needle assembly of FIG. 16 taken along line 17—17.

Turning to FIGS. 16 and 17, in an alternative embodiment of the present invention, sleeve 60 includes a flange 61 projecting radially outwardly from the proximal end of the sleeve. This flange prevents sleeve 60 from being forced all the way through the stopper when the sleeve is being pushed into the stopper and during use when the sleeve is in the stopper. Flange 61 also provides more contact surface on the sleeve in area 62 where it contacts forward end 22 of the hub or epoxy 29 to reduce the stresses developed at this contact area, while the sleeve is being pushed through the stopper. These lower stresses reduce the possibility that the epoxy or hub will be damaged in such a way as to generate particulate contamination.

Figure 18:
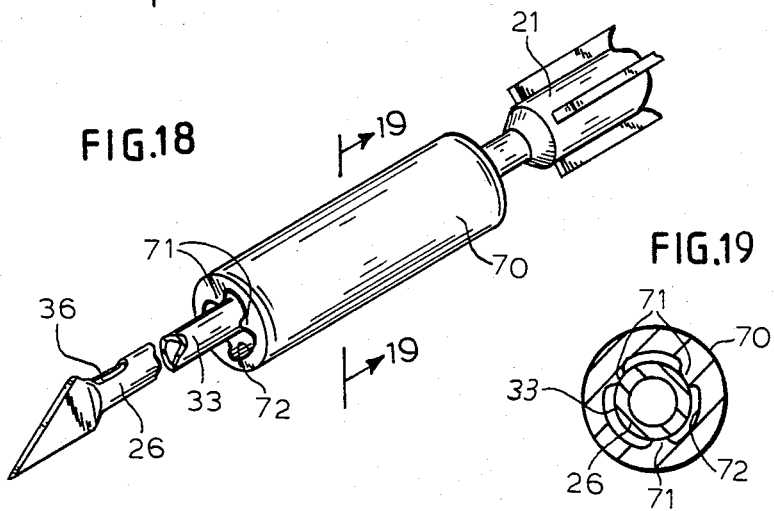
FIG. 18 is an enlarged partial perspective view of another alternative embodiment of the self-venting, non-coring needle assembly.
Figure 19:
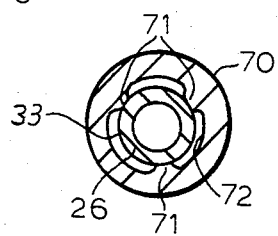
FIG. 19 is a cross-sectional view of the self-venting, non-coring needle assembly of FIG. 18 taken along line 19—19.

Adverting to FIGS. 18 and 19, in another alternative embodiment of the present invention, sleeve 70 includes spaced projections 71 extending radially inwardly from inside diameter 72. These projections contact outside diameter 33 of cannula 26 creating a frictional interference fit between the sleeve and the cannula that is sufficient to support the weight of the hub and cannula when the sleeve is held in a vertical orientation. Accordingly, additional force is required to move the cannula upwardly or downwardly with respect to the sleeve. The frictional fit between sleeve 70 and cannula 26 is desirable in applications where the instant invention is connected to tubing, and the other end of the tubing connected to a syringe or other fluid moving device. In these applications, the needle assembly (not shown) can be assembled to a vial with a pierceable stopper (not shown) and then the length of cannula 26 in the vial and therefore the height of aperture 36 can be adjusted by lifting up and pushing down on the needle. This is a desirable feature since the aperture can be positioned lower in the vial when fluids are being withdrawn and higher when fluids are being added. The frictional fit will help keep the needle at the desired position.

It is also within the purview of this invention to include a needle assembly wherein the sleeve member is fixedly attached to the cannula and not slidably engaged thereon. An embodiment with a fixed sleeve may be desirable, for example, when the needle assembly is used primarily for withdrawing fluid from a container having a needle penetrable stopper. In order to withdraw liquid, the aperture in the cannula should be below the liquid level in the container. Accordingly, fixing the sleeve member to the cannula at the proximal end of the cannula will result in the aperture being located as far as possible from the sleeve and, therefore, as deep as possible into the container. An embodiment with a fixed sleeve may be constricted as shown in FIGS. 18 and 19 wherein projections 71 are made large enough so that the contact between the projections and cannula 26 creates a frictional fit which will hold the sleeve member in a relative fixed position with respect to the cannula during normal use. Also, adhesive may be used to connect the sleeve member to the cannula.

A wide variety of rigid materials are suitable for constructing the hub, however, thermoplastic materials such as polypropylene and polyethylene are preferred. It is preferred that the cannula and sleeve be constructed of a medical grade stainless steel except where the sleeve contains spaced projections extending radially inwardly from the inside diameter. With the latter sleeve construction, thermoplastic materials such as polypropylene, polytetrafluoroethylene and polyethylene are preferred. With respect to joining the cannula to the hub, a wide variety of medical grade epoxy resins is commercially available. The choice of epoxy formulation is dictated by the materials and processing conditions chosen for the needle assembly. If the cannula and the hub are made in one piece, thermoplastic materials such as ABS, polyproplylene and polyethylene are preferred. It may also be desirable to apply a medical grade lubricant, such as medical grade silicon lubricant, to the outside of the cannula to reduce the force required for cannula penetration of the stopper. It is preferred that all elements of the self-venting, non-coring needle assembly should be sterile when used. Accordingly, materials should be selected for compatability with the sterilization process being used.

Thus it can be seen that the present invention provides a simple, straight forward, easily fabricated self-venting, non-coring needle assembly which allows transfer of liquid to and from a vial with a pierceable stopper while incurring minimal stopper damage and requiring minimal penetration forces. The present invention is also operable without the use of external apparatus which is not part of the fluid path.

What is claimed is:

1. A self-venting, non-coring needle assembly for the transfer of liquid to or from a container having a needle penetrable stopper thereon comprising:
    a rigid hub having a forward end, a rearward end adapted to engage external fluid transfer apparatus and a passageway therethrough;
    a cannula extending outwardly from said forward end and terminating in a closed distal end means for penetrating said stopper, said cannula having a lumen in fluid communication with said passageway, said cannula having an aperture in the side thereof adjacent to said distal end and in fluid communication with said lumen;
    a sleeve member slidably engaged on said cannula and being shorter in length than the distance between said aperture and said forward end of said hub, said sleeve member adapted to enter the hole in the needle penetrable stopper made by said distal end means;
    venting means for allowing gas to pass between the outside of said cannula and the inside of said sleeve; and
    retention means for preventing said sleeve from sliding off said cannula.

2. The needle assembly of claim 1 wherein said cannula has a circularly shaped cross section.

3. The needle assembly of claim 2 wherein said sleeve member has a circularly shaped cross-section.

4. The needle assembly of claim 3 wherein said sleeve member further contains a flange extending radially outwardly from the end of said sleeve member facing said hub.

5. The needle assembly of claim 1 wherein said distal end includes a flat portion extending substantially parallel to the longitudinal axis of said cannula.

6. The needle assembly of claim 1 wherein said cannula is made of stainless steel.

7. The needle assembly of claim 1 wherein said sleeve member is made from material selected from the group of stainless steel and thermoplastic materials.

8. A self-venting, non-coring needle assembly for the transfer of liquid to or from a container having a needle penetrable stopper thereon comprising:
    a rigid hub having a forward end, a rearward end adapted to engage external fluid transfer apparatus and a passageway therethrough;
    a cannula extending outwardly from said forward end and terminating in a closed distal end, said cannula having a lumen in fluid communication with said passageway, said distal end including a flat portion for penetrating said stopper extending substantially parallel to the longitudinal axis of said cannula, said flat portion terminating at a straight edge lying at an angle to the longitudinal axis of said cannula, said cannula having an aperture in the side thereof adjacent to said distal end and in fluid communication with said lumen;
    a sleeve member slidably engaged on said cannula and being shorter in length than the distance between said aperture and said forward end of said hub, said sleeve member adapted to enter the hole in the needle penetrable stopper made by said flat portion;
    venting means for allowing gas to pass between the outside of said cannula and the inside of said sleeve; and
    retention means for preventing said sleeve from sliding off said cannula.

9. The needle assembly of claim 8 wherein the lesser included angle between said straight edge and the longitudinal axis of said cannula is within the range of about 20 to 60 degrees.

10. The needle assembly of claim 8 wherein said flat portion is tapered in a direction toward said straight edge in a razor-like fashion.

11. The needle assembly of claim 8 wherein said aperture is positioned substantially in alignment with said straight edge.

12. A self-venting, non-coring needle assembly for the transfer of liquid to or from a container having a needle penetrable stopper thereon comprising:
    a rigid hub having a forward end, a rearward end adapted to engage external fluid transfer apparatus and a passageway therethrough;
    a cannula extending outwardly from said forward end and terminating in a closed distal end means for penetrating said stopper, said cannula having a lumen in fluid communication with said passageway, said cannula having an aperture in the side thereof adjacent to said distal end and in fluid communication with said lumen, said cannula having a circularly shaped cross section;
    a circularly shaped sleeve member slidably engaged on said cannula and being shorter in length than the distance between said aperture and said forward end of said hub, said sleeve member adapted to enter the hole made by said distal end means;
    venting means includes a circularly shaped space between the outside diameter of said cannula and the larger inside diameter of said sleeve member for allowing gas to pass between the outside of said cannula and the inside of said sleeve; and
    retention means for preventing said sleeve from sliding off said cannula.

13. The needle assembly of claim 10 further including a plurality of spaced projections extending radially inwardly from the inside diameter of said sleeve member, said projection contacting the outside diameter of said cannula creating a frictional interference fit between said sleeve member and said cannula, said interference fit being sufficient to support the weight of said hub and said cannula so that when said sleeve member is oriented and held in a vertical direction, additional outside force is required to move said cannula with respect to said sleeve member.

14. A self-venting, non-coring needle assembly for the transfer of liquid to or from a container having a needle penetrable stopper thereon comprising:
- a rigid hub having a forward end, a rearward end adapted to engage external fluid transfer apparatus and a passageway therethrough;
- a cannula extending outwardly from said forward end and terminating in a closed distal end, said cannula having a lumen in fluid communication with said passageway, said distal end including a flat portion for penetrating said slopper extending substantially parallel to the longitudinal axis of the cannula, said cannula having an aperture in the side thereof adjacent to said distal end and in fluid communication with said lumen;
- a sleeve member slidably engaged on said cannula and being shorter in length than the distance between said aperture and said forward end of said hub, said sleeve member adapted to enter the hole made by said flat portion;
- venting means for allowing gas to pass between the outside of said cannula and the inside of said sleeve; and
- retention means for preventing said sleeve from sliding off said cannula including said flat portion being larger along its major axis than the inside dimension of said sleeve member and said hub being larger than the inside dimension of said sleeve member so that said sleeve member is prevented from sliding off said cannula.

15. A self-venting, non-coring needle assembly for the transfer of liquid to or from a container having a needle penetrable stopper thereon comprising:
- a hub having a forward end, a rearward end adapted to engage external fluid transfer apparatus and a passageway therethrough;
- a hollow shaft extending outwardly from said forward end and having a lumen in fluid communication with said passageway, said shaft having a closed distal end means for penetrating said stopper and having an aperture in the side thereof near said distal end and in fluid communication with said lumen;
- a sleeve slidably maintained on said shaft and adapted to enter the hole in the needle penetrable stopper made by said distal end means; and
- venting means for allowing gas to pass between the outside of said shaft and the inside of said sleeve.

16. A self-venting, non-coring needle assembly for the transfer of liquid to or from a container having a needle penetrable stopper thereon comprising:
- a rigid hub having a forward end, a rearward end adapted to engage external fluid transfer apparatus and a passageway therethrough;
- a cannula extending outwardly from said forward end and terminating in a closed distal end, said cannula having a lumen in fluid communication with said passageway, said distal end including a flat portion extending substantially parallel to the longitudinal axis of said cannula, said flat portion being larger along its major dimension than the outside diameter of said cannula and terminating at a straight edge lying at an angle to the longitudinal axis of said cannula, said cannula having an aperture in the side thereof adjacent to said distal end and in fluid communication with said lumen; and
- a circularly shaped sleeve member surrounding said cannula and slidably engaged thereon, said sleeve member being shorter in length than the distance between said aperture and said forward end of said hub, said sleeve member having an inside diameter larger than the outside diameter of said cannula to allow gas to pass therebetween and smaller than said flat portion along its major axis so that said sleeve is prevented from sliding off said distal end of said cannula, said inside diameter of said sleeve member being smaller than said hub so that said sleeve is prevented from sliding off said cannula at its proximal end.

17. The needle assembly of claim 16 wherein said flat portion is tapered in a direction toward said straight edge in a razor-like fashion.

18. The needle assembly of claim 16 wherein said aperture is positioned substantially in alignment with said straight edge.

19. The needle assembly of claim 16 further including at least three spaced projections extending radially inwardly from the inside diameter of said sleeve member, said projections contacting the outside diameter of said cannula creating a frictional interference fit between said sleeve member and said cannula, said interference fit being sufficient to support the weight of said hub and said cannula so that when said sleeve member is oriented and held in a vertical direction additional, outside force is required to move said cannula with respect to said sleeve member.

20. A self-venting, non-coring needle assembly for the transfer of liquid to or from a container having a needle penetrable stopper thereon comprising:
- a hub having a forward end, a rearward end adapted to engage external fluid transfer apparatus and a passageway therethrough;
- a hollow shaft extending outwardly from said forward end and having a lumen in fluid communication with said passageway, said shaft having a closed distal end means for penetrating said stopper and having an aperture in the side thereof near said distal end and in fluid communication with said lumen;
- a sleeve fixedly maintained on the proximal end of said shaft and adapted to enter the hole in the needle penetrable stopper made by said distal end means; and
- venting means for allowing gas to pass between the outside of said shaft and the inside of said sleeve.

* * * * *